US009404107B2

(12) United States Patent
Han et al.

(10) Patent No.: US 9,404,107 B2
(45) Date of Patent: Aug. 2, 2016

(54) **INTEGRATION OF GENES INTO THE CHROMOSOME OF *SACCHAROPOLYSPORA SPINOSA***

(75) Inventors: Lei Han, Carmel, IN (US); Nigel Mouncey, Indianapolis, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 27 days.

(21) Appl. No.: 13/100,220

(22) Filed: May 3, 2011

(65) Prior Publication Data

US 2012/0282624 A1 Nov. 8, 2012

(51) Int. Cl.

| | |
|---|---|
| *C12P 21/06* | (2006.01) |
| *C12N 15/75* | (2006.01) |
| *C12N 15/10* | (2006.01) |
| *C12P 19/62* | (2006.01) |
| *C12P 21/00* | (2006.01) |
| *C12N 15/52* | (2006.01) |
| *C12N 15/90* | (2006.01) |

(52) U.S. Cl.
CPC ............ *C12N 15/1037* (2013.01); *C12N 15/52* (2013.01); *C12N 15/905* (2013.01); *C12P 19/62* (2013.01); *C12P 21/00* (2013.01)

(58) Field of Classification Search
CPC .. C12N 15/1037; C12N 15/52; C12N 15/905; C12P 19/62; C12P 21/00
See application file for complete search history.

(56) References Cited

U.S. PATENT DOCUMENTS 5,362,634 A 11/1994 Boeck et al.
5,670,486 A 9/1997 Mynderse et al.

FOREIGN PATENT DOCUMENTS

| | | | |
|---|---|---|---|
| CN | 1986768 | A | 6/2007 |
| WO | 8903883 | A1 | 5/1989 |
| WO | WO93/09126 | | 5/1993 |
| WO | 9946387 | A1 | 9/1999 |
| WO | 0116303 | A2 | 3/2001 |
| WO | 03070908 | A2 | 8/2003 |
| WO | WO 2010-149956 | | 12/2010 |

OTHER PUBLICATIONS

Madduri et al., Genes for the biosynthesis of spinosyns: applications for yield improvement in Saccharopolyspora spinosa, Journal of Industrial Microbiology & Biotechnology (2001) 27, 399-402.*

Zirkle et al., Analysis of a I08-kb Region of the Saccharopolyspora spinosa Genome Covering the Obscurin Polyketide Synthase Locus, DNA Sequence, Apr. 2004 vol. 15 (2). pp. 123-134.*

(Continued)

*Primary Examiner* — Reza Ghafoorian

(74) *Attorney, Agent, or Firm* — Yung H. Lee; Magleby Cataxinos & Greenwood

(57) ABSTRACT

This invention includes a process for the identification and validation of a neutral polynucleotide integration site within the *S. spinosa* genome. In addition, the invention includes the use of the neutral site and methods for the integration of a polynucleotide containing a gene expression cassette, which is stably maintained and expressed over subsequent generations. The invention includes neutral integration sites that can be disrupted without negatively impacting spinosyn production, growth or other desired metabolic characteristics.

10 Claims, 2 Drawing Sheets

(56) References Cited

OTHER PUBLICATIONS

Waldron et al., Cloning and analysis of the spinosad biosynthetic gene cluster of Saccharopolyspora spinosa, Chemistry & Biology 8 (2001) 487-499.*

Sheehan et al., Engineering of the spinosyn PKS: Directing starter unit incorporation, J. Nat. Prod. 2006, 69, 1702-1710.*

Shaw et al., Molecular genetics of aminoglycoside resistance genes and familiar relationships of the aminoglycoside-modifying enzymes, Microbiological Reviews, Mar. 1993, p. 138-163.*

Ke-Xue, Huang et al., "Recent advances in the biochemistry of spinosyns," Applied Microbiology and Biotechnology, Dec. 10, 2008, pp. 13-23, vol. 82, No. 1.

Kirst, H. A., et al., "Discovery, isolation, and structure elucidation of a family of structurally unique, fermentation-derived tetracyclic macrolides," Water Soluble Polymers: Synthesis, Solution Properties and Applications, American Chemical Society, Jan. 1, 1992, pp. 214-225.

Waldron, C., et al., "A cluster of genes for the biosynthesis of spinosyns, novel macrolide insect control agents produced by saccharopolyspora spinosa," Antonie Van Leeuwenhoek, Dordrecht, NL, Dec. 1, 2000, pp. 385-390, vol. 78, No. 3/4.

Zirkle, Ross et al., "Analysis of a 108-kb region of the *Saccharopolysproa spinosa* genome covering the obscuring polyketide synthase locus," DNA Sequence: The Journal of DNA Sequencing and Mapping, Apr. 2004, pp. 123-134, vol. 15, No. 4.

Matsushima et al., "Conjugal transfer of cosmid DNA form *Escherichia coli* to Saccharopolyspora spinosa: effects of chromosomal insertions on macrolide A83543 production," Gene, 1994, pp. 39-45, vol. 146.

Pulido et al., "Optimization of gene expression in Streptomyces lividans by a transcription terminator," Nucleic Acids Research, 1987, pp. 4227-4240, vol. 15, No. 10.

Xia et al., "Construction and functional analysis of engineering bacteria for spinosa-producing," Conference abstract 15th International Symposium on the Biology of Actinomycetes, Aug. 20-25, 2009, Shanghai, China.

Gust et al, "PCR-targeted streptomyces gene replacement identifies a protein domain needed for biosynthesis of the sesquiterpene soil odor geosmin," PNAS, Feb. 18, 2003, pp. 154-1546, vol. 100, No. 4.

GenBank accession No. AY007564.1, <<www.ncbi.nlm.nih.gov/nuccore/13162633?report=genbank&sat=4&from=21111&to=28898, May 16, 2001, 4 pages.

GenBank accession No. AY466441.1, <<www.ncbi.nlm.nih.gov/nuccore/41350128>>, Apr. 29, 2005, 37 pages.

Results for job emboss_needle-I20131218-173848-0676-1033240-oy, Dec. 18, 2013, 28 pages.

* cited by examiner

INTEGRATION OF GENES INTO THE CHROMOSOME OF *SACCHAROPOLYSPORA SPINOSA*

FIELD OF THE INVENTION

The invention applies to the technical field of molecular genetics wherein genes may be integrated into the chromosome of *Saccharopolyspora spinosa*. A key metabolic engineering approach is the integration and expression of target genes at chromosomal DNA regions that result in little to no negative impact on spinosyn production or growth.

BACKGROUND

As disclosed in U.S. Pat. No. 5,362,634, fermentation product A83543 is a family of related compounds produced by *Saccharopolyspora spinosa*. The known members of this family have been referred to as factors or components, and each has been given an identifying letter designation. These compounds are hereinafter referred to as spinosyn A, B, etc. The spinosyn compounds are useful for the control of arachnids, nematodes and insects, in particular, Lepidoptera and Diptera species. The compounds are considered environmentally friendly with an appealing toxicological profile.

The naturally produced spinosyn compounds are macrolides consisting of a 21-carbon tetracyclic lactone to which are attached two deoxysugars, a neutral sugar (rhamnose) and an amino sugar (forosamine) (see Kirst et al. (1991). If the amino sugar is not present, the compounds have been referred to as the pseudoaglycone of A, D, etc., and if the neutral sugar is not present then the compounds have been referred to as the reverse pseudoaglycone of A, D, etc. A more preferred nomenclature is to refer to the pseudoaglycones as spinosyn A 17-Psa, spinosyn D 17-Psa, etc., and to the reverse pseudoaglycones as spinosyn A 9-Psa, spinosyn D 9-Psa, etc.

The naturally produced spinosyn compounds may be produced via fermentation from *S. spinosa* strains NRRL 18395, 18537, 18538, 18539, 18719, 18720, 18743 and 18823 and derivatives therefrom. These cultures have been deposited and made part of the stock culture collection of the Midwest Area Northern Regional Research Center, Agricultural Research Service, United States Department of Agriculture, 1815 North University Street, Peoria, Ill., 61604.

U.S. Pat. No. 5,362,634 and corresponding European Patent No. 0375316 B1 relate to spinosyns A, B, C, D, E, F, G, H, and J. These compounds are said to be produced by culturing a strain of the novel microorganism *Saccharopolyspora spinosa* selected from NRRL 18395, NRRL 18537, NRRL 18538, and NRRL 18539.

WO 93/09126 relates to spinosyns L, M, N, Q, R, S, and T. Also discussed therein are two spinosyn J producing strains: NRRL 18719 and NRRL 18720, and a strain that produces spinosyns Q, R, S, and T: NRRL 18823.

WO 94/20518 and U.S. Pat. No. 5,670,486 relates to spinosyns K, O, P, U, V, W, and Y, and derivatives thereof. Also discussed therein is spinosyn K-producing strain NRRL 18743.

A challenge in producing spinosyn compounds arises from the need to identify and validate neutral sites in the *S. spinosa* genome, wherein a polynucleotide containing a gene expression cassette could be integrated and stably expressed. The introduced gene expression cassette can contain biosynthetic genes that provide a method for producing new derivatives of the spinosyns which may have a different spectrum of insecticidal activity or a gene expression cassette which can increase the titer levels of spinosyns, in addition to other gene expression cassettes which would impart new beneficial characteristics to the existing spinosyn production strains. It would be advantageous to identify and introduce genes, which result in increased production of spinosyn compounds. It would also be advantageous to utilize neutral sites, wherein stable integration results in little to no negative impact on spinosyn production, growth or other desired metabolic characteristics.

SUMMARY OF THE INVENTION

The present invention provides processes for identifying and validating neutral sites in the *S. spinosa* genome, wherein novel polynucleotide(s) containing at least one gene expression cassette which can be integrated and stably expressed.

Some of the embodiments of the invention include the identification and validation of neutral sites in the *S. spinosa* genome, wherein novel polynucleotide(s) containing at least one gene expression cassette can be integrated and stably expressed over subsequent generations.

Embodiments of the present invention can also include using the obscurin polyketide synthase (PKS) locus as a neutral site for integration of a polynucleotide containing a gene expression cassette, either foreign or native, within the genome of *S. spinosa*. More specifically the obsA gene of the obscurin polyketide synthase (PKS) locus can be disrupted without negatively impacting spinosyn production, growth or other desired metabolic characteristics.

Additional methods of the present invention include polynucleotide integration into chromosomal DNA of *S. spinosa* species, which are useful for the production of insecticides, integrants thereof, and also to the use of the integrants.

Some of the embodiments of the present invention can include methods for identifying any neutral site within the *S. spinosa* genome and the integration of a polynucleotide containing a gene expression cassette, which is stably expressed.

Other embodiments of the present invention can include integrating a polynucleotide into the *S. spinosa* genome without negatively impacting spinosyn production, growth or other desired metabolic characteristics Other embodiments of the present invention can include integrating a polynucleotide containing a gene expression cassette into the *S. spinosa* genome, the expression of which results in increased spinosyn production.

DETAILED DESCRIPTION OF THE INVENTION

Figure 1:
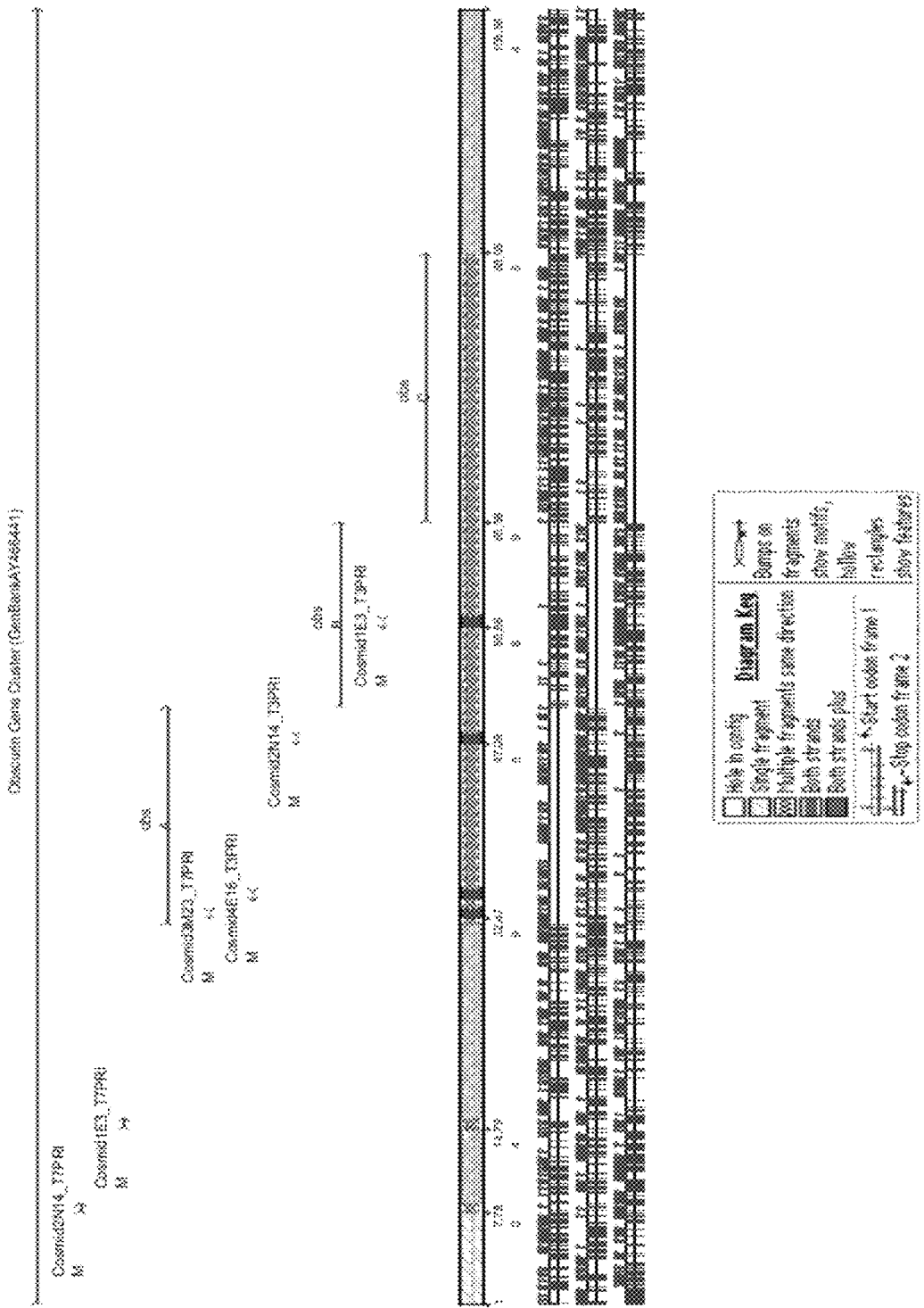
FIG. 1 depicts mapping of the end sequence of the cosmid clones onto the obscurin gene cluster. The overlapping cosmid clones are shown. Solid bars indicate the actual size of the inserts in cosmid clone 1E3 and cosmid clone 2N14 relative to the obscurin gene cluster. The dotted lines indicate that only one end of the cosmid is within the obscurin gene cluster.

Molecular tools useful for metabolic engineering for spinosyn strain improvement include the identification and validation of neutral sites in the *S. spinosa* genome where gene expression cassettes can be introduced. Neutral sites are defined as DNA regions in the genome, which have little to no negative impact on the primary metabolic activities of *S. spinosa*, spinosyn production and other desired characteristics. The identified neutral sites are intended for stable integration and expression of target genes either native or heterologous to *S. spinosa* which can include i) introducing beneficial characteristics to the existing spinosyn production strains such as expression of a heterologous hemoglobin gene; ii) improving specific characteristics of the existing spinosyn production strains (e.g. improving the bioconversion of pseudoaglycones to spinosyns); iii) introducing multiple copies of the same gene(s) at different neutral sites to maximize the benefit of the target gene(s) and to ensure the stability of the engineered recombinant strains; or iv) introducing multiple target genes to simultaneously de-bottleneck two or more rate-limiting steps controlling spinosyn biosynthesis and production. The secondary metabolic pathways in *S. spinosa*, non essential for the primary metabolic activities of the organism, represent an attractive source for neutral sites. Of these the non-spinosyn polyketide synthase gene clusters are of particular interest since disruption of the gene clusters may result in the elimination of potential competing pathways for the common acyl-CoA precursors and cofactors essential for spinosyn biosynthesis and production. This may create synergy between the benefits of the target genes and increased availability of the precursors.

There are many different uses for integrated genes within the chromosome of *Saccharopolyspora spinosa*. The cloned genes, either native or heterologous, can be used to improve yields of spinosyns and to produce new spinosyns. Improved yields can be obtained by integrating into the genome of a particular strain a duplicate copy of the gene to overcome an enzyme that is rate limiting in that strain. In some cases, where the biosynthetic pathway is blocked in a particular mutant strain due to lack of a required enzyme, production of the desired spinosyns can be restored by integrating a copy of the required gene. In other cases where a biosynthetic pathway is disrupted, a different precursor strain can be created.

The following definitions are used herein and should be referred to for interpretation of the claims and the specification. Unless otherwise noted, all U.S. patents and U.S. patent applications referenced herein are incorporated by reference in their entirety.

As used herein, the indefinite articles "a" and "an" preceding an element or component of the invention are intended to be nonrestrictive regarding the number of instances (i.e., occurrences) of the element or component. Therefore "a" or "an" should be read to include one or at least one, and the singular word form of the element or component also includes the plural unless the number is obviously meant to be singular.

As used herein, the terms "comprising" and "including" mean the presence of the stated features, integers, steps, or components as referred to in the claims, but that it does not preclude the presence or addition of one or more other features, integers, steps, components or groups thereof. This means a composition, a mixture, a process, a method, an article, or an apparatus that "comprises" or "includes" a list of elements is not limited to only those elements but may include others not expressly listed or inherent to it. As used herein, "or" refers to an inclusive and an exclusive "or". For example, a condition A or B is satisfied by any one of the following: A is true (or present) and B is false (or not present), A is false (or not present) and B is true (or present), and both A and B are true (or present).

As used herein, the term "about" refers to modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make, the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "invention" or "present invention" is a non-limiting term and is intended to encompass all possible variations as described in the specification and recited in the claims.

As used herein, the terms "polypeptide" and "peptide" will be used interchangeably to refer to a polymer of two or more amino acids joined together by a peptide bond. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics. The peptides may comprise L-amino acids.

As used herein, the terms "peptide of interest", "POI", "gene product", "target gene product", and "target coding region gene product" refer to the desired heterologous peptide/protein product encoded by the recombinantly expressed foreign gene. The peptide of interest may include any peptide/protein product including, but not limited to proteins, fusion proteins, enzymes, peptides, polypeptides, and oligopeptides. The peptide of interest ranges in size from 2 to 398 amino acids in length.

As used herein, the term "genetic construct" refers to a series of contiguous nucleic acids useful for modulating the genotype or phenotype of an organism. Non-limiting examples of genetic constructs include but are not limited to a nucleic acid molecule, and open reading frame, a gene, an expression cassette, a vector, a plasmid and the like.

As used herein, the term "endogenous gene" refers to a native gene in its natural location in the genome of an organism.

As used herein, a "foreign gene" refers to a gene not normally found in the host organism, but that is introduced into the host organism by gene transfer. Foreign genes can comprise native genes inserted into a non-native organism, or chimeric genes.

As used herein, the term "heterologous" with respect to sequence within a particular organism/genome indicates that the sequence originates from a foreign species, or, if from the same species, is substantially modified from its native form in composition and/or genomic locus by deliberate human intervention. Thus, for example, heterologous gene expression refers to the process of expressing a gene from one organism/genome by placing it into the genome of a different organism/genome.

As used herein, the term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

The term "genetically engineered" or "genetically altered" means the scientific alteration of the structure of genetic material in a living organism. It involves the production and use of recombinant DNA. More in particular it is used to delineate the genetically engineered or modified organism from the naturally occurring organism. Genetic engineering may be done by a number of techniques known in the art, such as e.g. gene replacement, gene amplification, gene disruption, transfection, transformation using plasmids, viruses, or other vectors. A genetically modified organism, e.g. genetically modified microorganism, is also often referred to as a recombinant organism, e.g. recombinant microorganism.

As used herein, the term "disrupted" or "disruption" when referring to a gene that has been manipulated or modified through genetic engineering or through natural causes that change the activity of a gene. Such gene activity may be increased or decreased. Additionally, such disruption may abolish protein function. To facilitate such a decrease, the copy number of the genes may be decreased, such as for instance by underexpression or disruption of a gene. A gene is said to be "underexpressed" if the level of transcription of said gene is reduced in comparison to the wild type gene. This may be measured by for instance Northern blot analysis quantifying the amount of mRNA as an indication for gene expression. As used herein, a gene is underexpressed if the amount of generated mRNA is decreased by at least 1%, 2%, 5% 10%, 25%, 50%, 75%, 100%, 200% or even more than 500%, compared to the amount of mRNA generated from a wild-type gene. Alternatively, a weak promoter may be used to direct the expression of the polynucleotide. In another embodiment, the promoter, regulatory region and/or the ribosome binding site upstream of the gene can be altered to achieve the reduced expression. The expression may also be reduced by decreasing the relative half-life of the messenger RNA. In another embodiment, the activity of the polypeptide itself may be decreased by employing one or more mutations in the polypeptide amino acid sequence, which decrease the activity. For example, altering the affinity of the polypeptide for its corresponding substrate may result in reduced activity. Likewise, the relative half-life of the polypeptide may be decreased. In either scenario, that being reduced gene expression or reduced activity, the reduction may be achieved by altering the composition of the cell culture media and/or methods used for culturing. "Reduced expression" or "reduced activity" as used herein means a decrease of at least 5%, 10%, 25%, 50%, 75%, 100%, 200% or even more than 500%, compared to a wild-type protein, polynucleotide, gene; or the activity and/or the concentration of the protein present before the polynucleotides or polypeptides are reduced. The activity of the obsA genomic locus may also be reduced by contacting the protein with a specific or general inhibitor of its activity. The terms "reduced activity", "decreased or abolished activity" are used interchangeably herein.

In another embodiment, the promoter, regulatory region and/or the ribosome binding site upstream of the gene can be altered to achieve increased expression. The overexpression may also be reduced by increasing the relative half-life of the messenger RNA. In another embodiment, the activity of the polypeptide itself may be increased by employing one or more mutations in the polypeptide amino acid sequence, which increased the activity. For example, altering the affinity of the polypeptide for its corresponding substrate may result in increased activity. Likewise, the relative half-life of the polypeptide may be increased. In either scenario, that being gene overexpression or increased activity, the increase may be achieved by altering the composition of the cell culture media and/or methods used for culturing. "Overexpression" or "increased activity" as used herein means an increase of at least 5%, 10%, 25%, 50%, 75%, 100%, 200% or even more than 500%, compared to a wild-type protein, polynucleotide, gene; or the activity and/or the concentration of the protein present before the polynucleotides or polypeptides are reduced. The activity of the obsA genomic locus may also be increased by contacting the protein with a specific or general inhibitor of its activity. The terms "Overexpression" and "increased activity" may be used interchangeably.

Expression "control sequences" refers collectively to promoter sequences, ribosome binding sites, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Recombination" refers to the reassortment of sections of DNA or RNA sequences between two DNA or RNA molecules. "Homologous recombination" occurs between two DNA molecules, which hybridize by virtue of homologous or complementary nucleotide sequences present in each DNA molecule.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 Overview of principles of hybridization and the strategy of nucleic acid probe assays, Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids, which have more than 100 complementary residues on a filter in a Southern or Northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) Molecular Cloning—A Laboratory Manual (2nd ed.) Vol. 1-3, Cold Spring Harbor Laboratory, Cold Spring Harbor Press, NY, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization. Nucleic acids, which do not hybridize to each other under stringent conditions are still substantially identical if the polypeptides which they encode are substantially identical.

This occurs, e.g., when a copy of a nucleic acid is created using the maximum codon degeneracy permitted by the genetic code.

The invention also relates to an isolated polynucleotide hybridizable under stringent conditions, preferably under highly stringent conditions, to a polynucleotide as of the present invention.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

In one embodiment, a nucleic acid of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence shown in this application or the complement thereof.

Another non-limiting example of stringent hybridization conditions are hybridization in 6× sodium chloride/sodium citrate (SSC) at about 45° C., followed by one or more washes in 1×SSC, 0.1% SDS at 50° C., preferably at 55° C. more preferably at 60° C. and even more preferably at 65° C.

Highly stringent conditions can include incubations at 42° C. for a period of several days, such as 2-4 days, using a labeled DNA probe, such as a digoxigenin (DIG)-labeled DNA probe, followed by one or more washes in 2×SSC, 0.1% SDS at room temperature and one or more washes in 0.5× SSC, 0.1% SDS or 0.1×SSC, 0.1% SDS at 65-68° C. In particular, highly stringent conditions include, for example, 2 h to 4 days incubation at 42° C. using a DIG-labeled DNA probe (prepared by e.g. using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

In some embodiments an isolated nucleic acid molecule of the invention that hybridizes under highly stringent conditions to a nucleotide sequence of the invention can correspond to a naturally-occurring nucleic acid molecule. As used herein, a "naturally-occurring" nucleic acid molecule refers to an RNA or DNA molecule having a nucleotide sequence that occurs in nature (e.g., encodes a natural protein).

A skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

A cloned fragment of DNA containing genes for spinosyn biosynthetic enzymes would enable duplication of genes coding for rate limiting enzymes in the production of spinosyns. This could be used to increase yield in any circumstance when one of the encoded activities limited synthesis of the desired spinosyn. A yield increase in spinosyn A/D was observed when genes linked to the spinosyn polyketide synthase were duplicated by integrating a cosmid containing them into *S. spinosa* (Madduri et al., 2001). In another example, a yield increase of this type was achieved in fermentations of *Streptomyces fradiae* by duplicating the gene encoding a rate-limiting methyltransferase that converts macrocin to tylosin (Baltz et al., 1997).

Specific intermediates (or their natural derivatives) could be synthesized by mutant strains of *S. spinosa* in which certain genes encoding enzymes for spinosyn biosynthesis have been disrupted. Such strains can be generated by integrating, via homologous recombination, a mutagenic plasmid containing an internal fragment of the target gene. Upon plasmid integration, two incomplete copies of the biosynthetic gene are formed, thereby eliminating the enzymatic function it encoded. The substrate for this enzyme, or some natural derivative thereof, should accumulate upon fermentation of the mutant strain. Such a strategy was used effectively to generate a strain of *Saccharopolyspora erythraea* producing novel 6-deoxyerythromycin derivatives (Weber & McAlpine, 1992).

Such strains could be generated by swapping the target region, via double crossover homologous recombination, with a mutagenic plasmid containing the new fragment between non-mutated sequences, which flank the target region. The hybrid gene would produce protein with altered functions, either lacking an activity or performing a novel enzymatic transformation. A new derivative would accumulate upon fermentation of the mutant strain. Such a strategy was used to generate a strain of *Saccharopolyspora erythraea* producing a novel anhydroerythromycin derivative (Donadio et al., 1993).

Spinosyn biosynthetic genes and related ORFs were cloned and the DNA sequence of each was determined. The cloned genes and ORFs are designated hereinafter as spnA, spnB, spnC, spnD, spnE, spnF, spnG, spnH, spnI, spnJ, spnK, spnL, spnM, spnN, spnO, spnP, spnQ, spnR, spnS, ORFL15, ORFL16, ORFR1, ORFR2, *S. spinosa* gtt, *S. spinosa* gdh, *S. spinosa* epi, and *S. spinosa* kre.

*Saccharapolyspora spinosa* produces a mixture of nine closely related compounds collectively called "spinosyns". Within the mixture, spinosyn A and D, known as spinosad, are the major components and have activity against key insect targets. Spinosyn J and L, two of the minor components within the spinosyn mixture, are the precursors for spinetoram, another spinosyn insecticide.

Spinosad is an insecticide produced by Dow AgroSciences (Indianapolis, Ind.) that is comprised mainly of approximately 85% spinosyn A and approximately 15% spinosyn D. Spinosyn A and D are natural products produced by fermentation of *Saccharopolyspora spinosa*, as disclosed in U.S. Pat. No. 5,362,634. Spinosad is an active ingredient of several insecticidal formulations available commercially from Dow AgroSciences, including the TRACER™, SUCCESS™, SPINTOR™, and CONSERVE™ insect control products. For example, the TRACER product is comprised of about 44% to about 48% spinosad (w/v), or about 4 pounds of spinosad per gallon. Spinosyn compounds in granular and liquid formulations have established utility for the control of arachnids, nematodes, and insects, in particular Lepidoptera, Thysanoptera, and Diptera species. Spinosyn A and D is also referred to herein as Spinosyn A/D.

Spinetoram is a mixture of 5,6-dihydro-3'-ethoxy spinosyn J (major component) and 3'-ethoxy spinosyn L produced by Dow AgroSciences. The mixture can be prepared by ethoxylating a mixture of spinosyn J and spinosyn L, followed by hydrogenation. The 5,6 double bond of spinosyn J and its 3'-ethoxy is hydrogenated much more readily than that of spinosyn L and its 3'-ethoxy derivative, due to steric hindrance by the methyl group at C-5 in spinosyn L and its 3'-ethoxy derivative. See, U.S. Pat. No. 6,001,981. Spinosyn J and L is also referred to herein as Spinosyn J/L.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

In certain embodiments for improving S. spinosa strain improvement, stable transformants of polynucleotide(s) were produced by integrating a gene expression cassette into the genome of S. spinosa. This was accomplished by integrating the gene via homologous recombination using a part of chromosomal DNA and an insertion element. Based on this recombination and as a result of application thereof, the aac (3) IV and vhb gene expression cassettes were separately integrated into the chromosome of S. spinosa at the obscurin polyketide synthase (PKS) locus resulting in the inactivation of a native gene, obsA.

Other embodiments of the present invention can include integrating a polynucleotide into the S. spinosa genome without negatively impacting spinosyn production, growth or other desired metabolic characteristics Additional embodiments of the present invention can include integrating a polynucleotide containing a gene expression cassette into the S. spinosa genome, the expression of which results in increased spinosyn production.

Embodiments of the present invention can also include integrating a polynucleotide into the S. spinosa genome at a neutral site, and the subsequent stacking of a second polynucleotide at the same location. Wherein, the neutral site within the S. spinosa is utilized as a preferred locus for introducing additional polynucleotides.

Other embodiments of the present invention can include integrating a polynucleotide containing a gene expression cassette into the S. spinosa genome at a neutral site, and the subsequent removal of a selectable marker expression cassette from the integrated polynucleotide. Wherein, the method used to remove the selectable marker expression cassette is a double crossing over method, an excision method using CRE-LOX, an excision method using FLP-FRT, or an excision method using the RED/ET RECOMBINATION® kit (Genebridges, Heidelberg, Germany), in addition to other excision methods known in the art.

Additional embodiments of the present invention can include integrating a polynucleotide into the S. spinosa genome at a neutral site as an alternative to the use of extraneous replicating plasmids. Wherein, one or more extraneous replicating plasmids are incompatible due to the presence of similar origins or replication, incompatibility groups, redundant selectable marker, or other gene elements. Wherein, one or more extraneous replicating plasmids are not functional in S. spinosa due to the specificity of the S. spinosa restriction modification system. Wherein, one or more extraneous replicating plasmids are not available, functional or readily transformable within S. spinosa.

Other embodiments of the present invention can include methods for increasing the efficiency of homologous recombination in a prokaryotic cell. Methods relying upon homologous recombination mediated by introduced enzymes, such as lambda red 'recombineering' and analogous approaches are useful in a limited number of bacterial classes, particularly Escherichia (Datsenko and Wanner (2000) Proc Natl Acad Sci USA. 97: 6640-5) and Salmonella. Methods relying upon site-specific recombination mediated by introduced enzymes, such as phage integrases, FLP/FRT or Cre/loxP may also be used, but are reliant on the presence of pre-existing sites within the target DNA (Wirth et al (2007) Current Opinions in Biotechnology 18, 411-419). Alternative methods exploit viruses or mobile elements, or their components (e.g. phage, transposons or mobile introns).

However, methods relying upon host-mediated homologous recombination are by far the most commonly-used type of chromosomal DNA modifications. In a typical microbial application of host-mediated homologous recombination, a plasmid with a single region of sequence identity with the chromosome is integrated into the chromosome by single-crossover integration, sometimes referred to as 'Campbell-like integration'. After such an event, genes on the introduced plasmid are replicated as part of the chromosome, which may be more rapid than the plasmid replication. Accordingly, growth in medium with selection for a plasmid-borne selectable marker gene may provide a selective pressure for integration. Campbell-like integration can be used to inactivate a chromosomal gene by placing an internal fragment of a gene of interest on the plasmid, so that after integration, the chromosome will not contain a full-length copy of the gene. The chromosome of a Campbell-like integrant cell is not stable, because the integrated plasmid is flanked by the homologous sequences that directed the integration. A further homologous recombination event between these sequences leads to excision of the plasmid, and reversion of the chromosome to wild-type. For this reason, it may be necessary to maintain selection for the plasmid-borne selectable marker gene to maintain the integrant clone.

An improvement on the basic single-crossover integration method of chromosomal modification can include double crossover homologous recombination, also referred to as allelic exchange, which involves two recombination events. The desired modified allele is placed on a plasmid flanked by regions of homology to the regions flanking the target allele in the chromosome ('homology arms'). A first integration event can occur in either pair of homology arms, leading to integration of the plasmid into the chromosome in the same manner as Campbell-like integration. After the first crossover event, the chromosome contains two alternative sets of homologous sequences that can direct a second recombination event. If the same sequences that directed the first event recombine, the plasmid will be excised, and the cell will revert to wild-type. If the second recombination event is directed by the other homology arm, a plasmid will be excised, but the original chromosomal allele will have been exchanged for the modified allele introduced on the plasmid; the desired chromosomal modification will have been achieved. As with Campbell-like integration, the first recombination event is typically detected and integrants isolated using selective advantage conferred by integration of a plasmid-borne selectable marker gene.

"Functional polymorphism" as used herein refers to a change in the base pair sequence of a gene that produces a qualitative or quantitative change in the activity of the protein encoded by that gene (e.g., a change in specificity of activity; a change in level of activity). The term "functional polymorphism" includes mutations, deletions and insertions.

In general, the step of detecting the polymorphism of interest may be carried out by collecting a biological sample containing DNA from the source, and then determining the presence or absence of DNA containing the polymorphism of interest in the biological sample.

Determining the presence or absence of DNA encoding a particular mutation may be carried out with an oligonucleotide probe labeled with a suitable detectable group, and/or by means of an amplification reaction such as a polymerase chain reaction or ligase chain reaction (the product of which amplification reaction may then be detected with a labeled oligonucleotide probe or a number of other techniques). Numerous different oligonucleotide probe assay formats are known which may be employed to carry out the present invention. See, e.g., U.S. Pat. No. 4,302,204 to Wahl et al.; U.S. Pat. No. 4,358,535 to Falkow et al.; U.S. Pat. No. 4,563,419 to Ranki et al.; and U.S. Pat. No. 4,994,373 to Stavrianopoulos et al.

Amplification of a selected, or target, nucleic acid sequence may be carried out by any suitable means. See generally, Kwoh et al., Am. Biotechnol. Lab. 8, 14-25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad. Sci. USA 86, 1173-1177 (1989)), self-sustained sequence replication (or "3SR") (see J. Guatelli et al., Proc. Natl. Acad. Sci. USA 87, 1874-1878 (1990)), the Qβ replicase system (see P. Lizardi et al., BioTechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). Polymerase chain reaction is generally preferred.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. Such probes may be from 5 to 500 nucleotides in length, preferably 5 to 250, more preferably 5 to 100 or 5 to 50 nucleic acids. When PCR conditions allow for amplification of all allelic types, the types can be distinguished by hybridization with an allelic specific probe, by restriction endonuclease digestion, by electrophoresis on denaturing gradient gels, or other techniques.

Ligase chain reaction (LCR) is also carried out in accordance with known techniques. See, e.g., R. Weiss, Science 254, 1292 (1991). In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

DNA amplification techniques such as the foregoing can involve the use of a probe, a pair of probes, or two pairs of probes which specifically bind to DNA containing the functional polymorphism, but do not bind to DNA that does not contain the functional polymorphism. Alternatively, the probe or pair of probes could bind to DNA that both does and does not contain the functional polymorphism, but produce or amplify a product (e.g., an elongation product) in which a detectable difference may be ascertained (e.g., a shorter product, where the functional polymorphism is a deletion mutation). Such probes can be generated in accordance with standard techniques from the known sequences of DNA in or associated with a gene linked to obsA or from sequences which can be generated from such genes in accordance with standard techniques.

It will be appreciated that the detecting steps described herein may be carried out directly or indirectly. Other means of indirectly determining allelic type include measuring polymorphic markers that are linked to the particular functional polymorphism, as has been demonstrated for the VNTR (variable number tandem repeats).

Molecular biology comprises a wide variety of techniques for the analysis of nucleic acid and protein sequences. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, Molecular Cloning: A Laboratory Manual, 2 Ed., Cold spring Harbor Laboratory Press, Cold Spring Harbor, N.Y., 1989).

Most of these techniques involve carrying out numerous operations (e.g., pipetting, centrifugation, and electrophoresis) on a large number of samples. They are often complex and time consuming, and generally require a high degree of accuracy. Many techniques are limited in their application by a lack of sensitivity, specificity, or reproducibility.

Nucleic acid hybridization analysis generally involves the detection of a very small number of specific target nucleic acids (DNA or RNA) with an excess of probe DNA, among a relatively large amount of complex non-target nucleic acids. A reduction in the complexity of the nucleic acid in a sample is helpful to the detection of low copy numbers (i.e. 10,000 to 100,000) of nucleic acid targets. DNA complexity reduction is achieved to some degree by amplification of target nucleic acid sequences. (See, M. A. Innis et al., PCR Protocols: A Guide to Methods and Applications, Academic Press, 1990, Spargo et al., 1996, Molecular & Cellular Probes, in regard to SDA amplification). This is because amplification of target nucleic acids results in an enormous number of target nucleic acid sequences relative to non-target sequences thereby improving the subsequent target hybridization step.

The hybridization step involves placing the prepared DNA sample in contact with a specific reporter probe at set optimal conditions for hybridization to occur between the target DNA sequence and probe. Hybridization may be performed in any one of a number of formats. For example, multiple sample nucleic acid hybridization analysis has been conducted in a variety of filter and solid support formats (See Beltz et al., Methods in Enzymology, Vol. 100, Part et al., Eds., Academic Press, New York, Chapter 19, pp. 266-308, 1985). One format, the so-called "dot blot" hybridization, involves the non-covalent attachment of target DNAs to a filter followed by the subsequent hybridization to a radioisotope labeled probe(s). "Dot blot" hybridization gained wide-spread use over the past two decades during which time many versions were developed (see Anderson and Young, in Nucleic Acid Hybridization—A Practical Approach, Hames and Higgins, Eds., IRL Press, Washington, D.C. Chapter 4, pp. 73-111, 1985). For example, the dot blot method has been developed for multiple analyses of genomic mutations (EPA 0228075 to Nanibhushan et al.) and for the detection of overlapping clones and the construction of genomic maps (U.S. Pat. No. 5,219,726 to Evans).

Additional techniques for carrying out multiple sample nucleic acid hybridization analysis include micro-formatted multiplex or matrix devices (e.g., DNA chips) (see M. Barinaga, 253 Science, pp. 1489, 1991; W. Bains, 10 Bio/Technology, pp. 757-758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 Bio/Technology, pp. 757-758, 1992). SBH makes use of all possible n-nucleotide oligomers (n-mers) to identify n-mers in an unknown DNA sample, which are subsequently aligned by algorithm analysis to produce the DNA sequence (See, Drmanac U.S. Pat. No. 5,202,231).

There are two formats for carrying out SBH. The first format involves creating an array of all possible n-mers on a support, which is then hybridized with the target sequence. The second format involves attaching the target sequence to a support, which is sequentially probed with all possible n-mers. Southern, (United Kingdom Patent Application GB 8810400, 1988; E. M. Southern et al., 13 Genomics 1008, 1992), proposed using the first format to analyze or sequence DNA. Southern identified a known single point mutation using PCR amplified genomic DNA. Southern also described a method for synthesizing an array of oligonucleotides on a solid support for SBH. Drmanac et al., (260 Science 1649-1652, 1993), used a second format to sequence several short (116 bp) DNA sequences. Target DNAs were attached to membrane supports ("dot blot" format). Each filter was sequentially hybridized with 272 labeled 10-mer and 1-mer oligonucleotides. Wide ranges of stringency conditions were used to achieve specific hybridization for each n-mer probe. Washing times varied from 5 minutes to overnight using temperatures from 0° C. to 16° C. Most probes required 3 hours of washing at 16° C. The filters had to be exposed from 2 to 18 hours in order to detect hybridization signals.

Generally, a variety of methods are available for detection and analysis of the hybridization events. Depending on the reporter group (fluorophore, enzyme, radioisotope, etc.) used to label the DNA probe, detection and analysis are carried out fluorimetrically, calorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. Thus, detection of hybridization events is dependent upon how specific and sensitive hybridization can be made. Concerning genetic analysis, several methods have been developed that have attempted to increase specificity and sensitivity.

One form of genetic analysis is analysis centered on elucidation of single nucleic acid polymorphisms or ("SNPs"). Factors favoring the usage of SNPs are their high abundance in the human genome (especially compared to short tandem repeats, (STRs)), their frequent location within coding or regulatory regions of genes (which can affect protein structure or expression levels), and their stability when passed from one generation to the next (Landegren et al., Genome Research, Vol. 8, pp. 769-776, 1998).

A SNP is defined as any position in the genome that exists in two variants and the most common variant occurs less than 99% of the time. In order to use SNPs as widespread genetic markers, it is crucial to be able to genotype them easily, quickly, accurately, and cost-effectively. Numerous techniques are currently available for typing SNPs (for review, see Landegren et al., Genome Research, Vol. 8, pp. 769-776, (1998), all of which require target amplification. They include direct sequencing (Carothers et al., BioTechniques, Vol. 7, pp. 494-499, 1989), single-strand conformation polymorphism (Orita et al., Proc. Natl. Acad. Sci. USA, Vol. 86, pp. 2766-2770, 1989), allele-specific amplification (Newton et al., Nucleic Acids Research, Vol. 17, pp. 2503-2516, (1989), restriction digestion (Day and Humphries, Analytical Biochemistry, Vol. 222, pp. 389-395, 1994), and hybridization assays. In their most basic form, hybridization assays function by discriminating short oligonucleotide reporters against matched and mismatched targets. Many adaptations to the basic protocol have been developed. These include ligation chain reaction (Wu and Wallace, Gene, Vol. 76, pp. 245-254, 1989) and minisequencing (Syvanen et al., Genomics, Vol. 8, pp. 684-692, 1990). Other enhancements include the use of the 5'-nuclease activity of Taq DNA polymerase (Holland et al., Proc. Natl. Acad. Sci. USA, Vol. 88, pp. 7276-7280, 1991), molecular beacons (Tyagi and Kramer, Nature Biotechnology, Vol. 14, pp. 303-308, 1996), heat denaturation curves (Howell et al., Nature Biotechnology, Vol. 17, pp. 87-88, 1999) and DNA "chips" (Wang et al., Science, Vol. 280, pp. 1077-1082, 1998).

An additional phenomenon that can be used to distinguish SNPs is the nucleic acid interaction energies or base-stacking energies derived from the hybridization of multiple target specific probes to a single target. (See, R. Ornstein et al., "An Optimized Potential Function for the Calculation of Nucleic Acid Interaction Energies", Biopolymers, Vol. 17, 2341-2360 (1978); J. Norberg and L. Nilsson, Biophysical Journal, Vol. 74, pp. 394-402, (1998); and J. Pieters et al., Nucleic Acids Research, Vol. 17, no. 12, pp. 4551-4565 (1989)). This base-stacking phenomenon is used in a unique format in the current invention to provide highly sensitive Tm differentials allowing the direct detection of SNPs in a nucleic acid sample.

Additional methods have been used to distinguish nucleic acid sequences in related organisms or to sequence DNA. For example, U.S. Pat. No. 5,030,557 by Hogan et al. disclosed that the secondary and tertiary structure of a single stranded target nucleic acid may be affected by binding "helper" oligonucleotides in addition to "probe" oligonucleotides causing a higher Tm to be exhibited between the probe and target nucleic acid. That application however was limited in its approach to using hybridization energies only for altering the secondary and tertiary structure of self-annealing RNA strands, which if left unaltered would tend to prevent the probe from hybridizing to the target.

With regard to DNA sequencing, K. Khrapko et al., Federation of European Biochemical Societies Letters, Vol. 256, no. 1,2, pp. 118-122 (1989), for example, disclosed that continuous stacking hybridization resulted in duplex stabilization. Additionally, J. Kieleczawa et al., Science, Vol. 258, pp. 1787-1791 (1992), disclosed the use of contiguous strings of hexamers to prime DNA synthesis wherein the contiguous strings appeared to stabilize priming. Likewise, L. Kotler et al., Proc. Natl. Acad. Sci. USA, Vol. 90, pp. 4241-4245, (1993) disclosed sequence specificity in the priming of DNA sequencing reactions by use of hexamer and pentamer oligonucleotide modules. Further, S. Parinov et al., Nucleic Acids Research, Vol. 24, no. 15, pp. 2998-3004, (1996), disclosed the use of base-stacking oligomers for DNA sequencing in association with passive DNA sequencing microchips. Moreover, G. Yershov et al., Proc. Natl. Acad. Sci. USA, Vol. 93, pp. 4913-4918 (1996), disclosed the application of base-stacking energies in SBH on a passive microchip. In Yershov's example, 10-mer DNA probes were anchored to the surface of the microchip and hybridized to target sequences in conjunction with additional short probes, the combination of which appeared to stabilize binding of the probes. In that format, short segments of nucleic acid sequence could be elucidated for DNA sequencing. Yershov further noted that in their system the destabilizing effect of mismatches was increased using shorter probes (e.g., 5-mers). Use of such short probes in DNA sequencing provided the ability to discern the presence of mismatches along the sequence being probed rather than just a single mismatch at one specified location of the probe/target hybridization complex. Use of longer probes (e.g., 8-mer, 10-mer, and 13-mer oligos) was less functional for such purposes.

An additional example of methodologies that have used base-stacking in the analysis of nucleic acids includes U.S. Pat. No. 5,770,365 by Lane et al., wherein is disclosed a method of capturing nucleic acid targets using a unimolecular capture probe having a single stranded loop and a double stranded region which acts in conjunction with a binding target to stabilize duplex formation by stacking energies.

The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced.

Novel spinosyns can also be produced by mutagenesis of the cloned genes, and substitution of the mutated genes for their unmutated counterparts in a spinosyn-producing organism. Mutagenesis may involve, for example: 1) deletion or inactivation of a ketoreductase, dehydratase or enoyl reductase (KR, DH, or ER) domain so that one or more of these functions is blocked and the strain produces a spinosyn having a lactone nucleus with a double bond, a hydroxyl group, or a keto group that is not present in the nucleus of spinosyn A (see Donadio et al., 1993); 2) replacement of an AT domain so that a different carboxylic acid is incorporated in the lactone nucleus (see Ruan et al., 1997); 3) addition of a KR, DH, or ER domain to an existing PKS module so that the strain produces a spinosyn having a lactone nucleus with a saturated bond, hydroxyl group, or double bond that is not present in the nucleus of spinosyn A; or 4) addition or subtraction of a complete PKS module so that the cyclic lactone nucleus has a greater or lesser number of carbon atoms. A hybrid PKS can be created by replacing the spinosyn PKS loading domain with heterologous PKS loading. See, e.g., U.S. Pat. No. 7,626,010. It has further been noted that spinosyns via modification of the sugars that are attached to the spinosyn lactone backbone can include modifications of the rhamnose and/or forosamine moiety or attachment of different deoxy sugars. The Salas group in Spain demonstrated that novel polyketide compounds can be produced by substituting the existing sugar molecule with different sugar molecules. Rodriguez et al. J. Mol. Microbiol. Biotechnol. 2000 July; 2(3):271-6. The examples that follow throughout the application help to illustrate the use of mutagenesis to produce a spinosyn with modified functionality.

The DNA from the spinosyn gene cluster region can be used as a hybridization probe to identify homologous sequences. Thus, the DNA cloned here could be used to locate additional plasmids from the *Saccharopolyspora spinosa* gene libraries, which overlap the region described here but also contain previously uncloned DNA from adjacent regions in the genome of *Saccharopolyspora spinosa*. In addition, DNA from the region cloned here may be used to identify non-identical but similar sequences in other organisms. Hybridization probes are normally at least about 20 bases long and are labeled to permit detection.

Various types of mutagenesis can be used in the invention for a variety of purposes. They include, but are not limited to, site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, crystal structure or the like.

The texts and examples found herein describe these procedures. Additional information is found in the following publications and references cited within: Ling et al., Approaches to DNA mutagenesis: an overview, Anal Biochem. 254(2): 157-178 (1997); Dale et al., Oligonucleotide-directed random mutagenesis using the phosphorothioate method, Methods Mol. Biol. 57:369-374 (1996); Smith, In vitro mutagenesis, Ann. Rev. Genet. 19:423-462 (1985); Botstein & Shortle, Strategies and applications of in vitro mutagenesis, Science 229:1193-1201 (1985); Carter, Site-directed mutagenesis, Biochem. J. 237:1-7 (1986); Kunkel, The efficiency of oligonucleotide directed mutagenesis, in Nucleic Acids & Molecular Biology (Eckstein, F. and Lilley, D. M. J. eds., Springer Verlag, Berlin) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382

(1987); Bass et al., Mutant Trp repressors with new DNA-binding specificities, Science 242:240-245 (1988); Methods in Enzymol. 100: 468-500 (1983); Methods in Enzymol. 154: 329-350 (1987); Zoller & Smith, Oligonucleotide-directed mutagenesis using M13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Improved enzymatic in vitro reactions in the gapped duplex DNA approach to oligonucleotide-directed construction of mutations, Nucl. Acids Res. 16: 7207 (1988); Fritz et al., Oligonucleotide-directed construction of mutations: a gapped duplex DNA procedure without enzymatic reactions in vitro, Nucl. Acids Res. 16: 6987-6999 (1988); Kramer et al., Point Mismatch Repair, Cell 38:879-887 (1984); Carter et al., Improved oligonucleotide site-directed mutagenesis using M13 vectors, Nucl. Acids Res. 13: 4431-4443 (1985); Carter, Improved oligonucleotide-directed mutagenesis using M13 vectors, Methods in Enzymol. 154: 382-403 (1987); Eghtedarzadeh & Henikoff, Use of oligonucleotides to generate large deletions, Nucl. Acids Res. 14: 5115 (1986); Wells et al., Importance of hydrogen-bond formation in stabilizing the transition state of subtilisin, Phil. Trans. R. Soc. Lond. A 317: 415-423 (1986); Nambiar et al., Total synthesis and cloning of a gene coding for the ribonuclease S protein, Science 223: 1299-1301 (1984); Sakamar and Khorana, Total synthesis and expression of a gene for the a-subunit of bovine rod outer segment guanine nucleotide-binding protein (transducin), Nucl. Acids Res. 14: 6361-6372 (1988); Wells et al., Cassette mutagenesis: an efficient method for generation of multiple mutations at defined sites, Gene 34:315-323 (1985); Grundstrom et al., Oligonucleotide-directed mutagenesis by microscale 'shot-gun' gene synthesis, Nucl. Acids Res. 13: 3305-3316 (1985); Mandecki, Oligonucleotide-directed double-strand break repair in plasmids of *Escherichia coli*: a method for site-specific mutagenesis, Proc. Natl. Acad. Sci. USA, 83:7177-7181 (1986); Arnold, Protein engineering for unusual environments, Current Opinion in Biotechnology 4:450-455 (1993); Sieber, et al., Nature Biotechnology, 19:456-460 (2001). W. P. C. Stemmer, Nature 370, 389-91 (1994); and, I. A. Lorimer, I. Pastan, Nucleic Acids Res. 23, 3067-8 (1995). Additional details on many of the above methods can be found in Methods in Enzymology Volume 154, which also describes useful controls for trouble-shooting problems with various mutagenesis methods.

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions×100). Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available on the internet at the accelrys website, more specifically at http://www.accelrys.com), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available on the internet at the accelrys website, more specifically at http://www.accelrys.com), using a NWSgapdna.CMP matrix and a gap weight of 40, 50, 60, 70 or 80 and a length weight of 1, 2, 3, 4, 5 or 6. In another embodiment, the percent identity between two amino acid or nucleotide sequences is determined using the algorithm of E. Meyers and W. Miller (CABIOS, 4: 11-17 (1989) which has been incorporated into the ALIGN program (version 2.0) (available on the internet at the vega website, more specifically ALIGN—IGH Montpellier, or more specifically at http://vega.igh.cnrs.fr/bin/align-guess.cgi) using a PAM120 weight residue table, a gap length penalty of 12 and a gap penalty of 4.

The nucleic acid and protein sequences of the present invention may further be used as a "query sequence" to perform a search against public databases to, for example, identify other family members or related sequences. Such searches may be performed using the BLASTN and BLASTX programs (version 2.0) of Altschul, et al. (1990) J. Mol. Biol. 215:403-10. BLAST nucleotide searches may be performed with the BLASTN program, score=100, word length=12 to obtain nucleotide sequences homologous to the nucleic acid molecules of the present invention. BLAST protein searches may be performed with the BLASTX program, score=50, word length=3 to obtain amino acid sequences homologous to the protein molecules of the present invention. To obtain gapped alignments for comparison purposes, Gapped BLAST may be utilized as described in Altschul et al., (1997) Nucleic Acids Res. 25 (17): 3389-3402. When utilizing BLAST and Gapped BLAST programs, the default parameters of the respective programs (e.g., BLASTX and BLASTN) may be used. (Available on the internet at the ncbi website, more specifically at www.ncbi.nlm.nih.gov).

Suitable expression vectors for use in the present invention include prokaryotic and eukaryotic vectors (e.g., plasmid, phagemid, or bacteriophage), include mammalian vectors and plant vectors. Suitable prokaryotic vectors include plasmids such as, but not limited to, those commonly used for DNA manipulation in *Actinomyces*, (for example pSET152, pOJ260, PIJ101, pJV1, pSG5, pHJL302, pSAM2, pKC1250. Such plasmids are disclosed by Kieser et al. ("Practical *Streptomyces* Genetics", 2000). Other suitable vectors can include plasmids such as those capable of replication in *E. coli* (for example, pBR322, ColE1, pSC101, PACYC 184, itVX, pRSET, pBAD (Invitrogen, Carlsbad, Calif.) and the like). Such plasmids are disclosed by Sambrook (cf. "Molecular Cloning: A Laboratory Manual," second edition, edited by Sambrook, Fritsch, & Maniatis, Cold Spring Harbor Laboratory, (1989)) and many such vectors are commercially available. *Bacillus* plasmids include pC194, pC221, pT127, and the like, and are disclosed by Gryczan (In: The Molecular Biology of the Bacilli, Academic Press, NY (1982), pp. 307-329). Suitable *Streptomyces* plasmids include pli101 (Kendall et al., J. Bacteriol. 169:4177-4183, 1987), and *Streptomyces* bacteriophages include but not limited to such as ψC31 (Chater et al., In: Sixth International Symposium on Actinomycetales Biology, Akademiai Kaido, Budapest, Hungary (1986), pp. 45-54). *Pseudomonas* plasmids are reviewed by John et al. (Rev. Infect. Dis. 8:693-704, 1986), and Izaki (Jpn. J. Bacteriol. 33:729-742, 1978).

Suppression of the expression of particular genes is an important tool both for research and for the development of genetically engineered organisms more fitted for a particular purpose. Gene silencing can be accomplished by the introduction of a transgene corresponding to the gene of interest in the antisense orientation relative to its promoter (see, e.g., Sheehy et al., Proc. Nat'l Acad. Sci. USA 85:8805 8808 (1988); Smith et al., Nature 334:724 726 (1988)), or in the sense orientation relative to its promoter (Napoli et al., Plant Cell 2:279 289 (1990); van der Krol et al., Plant Cell 2:291 299 (1990); U.S. Pat. No. 5,034,323; U.S. Pat. No. 5,231,020; and U.S. Pat. No. 5,283,184), both of which lead to reduced expression of the transgene as well as the endogenous gene.

Posttranscriptional gene silencing has been reported to be accompanied by the accumulation of small (20 to 25 nucleotide) fragments of antisense RNA, which can be synthesized from an RNA template and represent the specificity and mobility determinants of the process (Hamilton & Baulcombe, Science 286:950 952 (1999)). It has become clear that in a range of organisms the introduction of dsRNA (double-stranded RNA) is an important component leading to gene silencing (Fire et al., Nature 391:806 811 (1998); Timmons & Fire, Nature 395:854 (1998); WO99/32619; Kennerdell & Carthew, Cell 95:1017 1026 (1998); Ngo et al., Proc. Nat'l Acad. Sci. USA 95:14687 14692 (1998); Waterhouse et al., Proc. Nat'l Acad. Sci. USA 95:13959 13964 (1998); WO99/53050; Cogoni & Macino, Nature 399:166 169 (1999); Lohmann et al., Dev. Biol. 214:211 214 (1999); Sanchez-Alvarado & Newmark, Proc. Nat'l Acad. Sci. USA 96:5049 5054 (1999)). In bacteria the suppressed gene does not need to be an endogenous bacterial gene, since both reporter transgenes and virus genes are subject to posttranscriptional gene silencing by introduced transgenes (English et al., Plant Cell 8:179 188 (1996); Waterhouse et al, supra). However, in all of the above cases, some sequence similarity may be preferred between the introduced transgene and the gene that is suppressed.

The present invention is explained in greater detail in the following non-limiting examples.

EXAMPLES

Identification of Cosmid Clones Carrying the Obscurin PKS Gene obsA

Screening of a cosmid library was completed using an 806-bp probe from the obsA genomic locus of *S. spinosa* (SEQ ID NO: 1). A cosmid library was constructed from a *S. spinosa* strain by BioS&T (Montreal, Canada) using Supercos I cosmid vector (Stratagene, La Jolla, Calif.) and the genomic DNA from the *S. spinosa* strain which was prepared according to the genomic DNA isolation protocol described by Kieser et al. (2000).

The screening of the library with the obsA probe allowed for the identification of cosmid clones carrying the 5' end of obsA under stringent conditions. Probe labeling, hybridization and detection were carried out using DIG DNA Labeling Kit and the DIG Nucleic Acid Detection Kit (Roche, Basel, Switzerland) according to manufacturer's instructions. Specifically, the 806-bp PCR fragment derived from the 5' end of obsA was labeled using the Random Prime Labeling Kit (Roche). Hybridization was carried out overnight at 58° C. in the hybridization oven followed by washing both filters twice at 65° C. for a total of 30 minutes using the wash buffer containing 0.1×SSC and 0.1% SDS. The hybridized probe was detected using Roche's DIG Nucleic Acid Detection kit based on the enzyme-linked immunoassay with a highly specific anti-DIG-AP antibody conjugate and the color substrates NBT (nitro blue tetrazolium) and BCIP (5-Bromo-4-chloro-3-indolyl phosphate). Several sets of cosmids with strong hybridization signals were identified. Four of the clones, 1E3, 2N14, 3M23 and 4E16, were selected for cosmid DNA isolation and sequencing confirmation.

PCR Amplification of the cosmid clones using obsA Forward Primer (SEQ ID NO:2 5'-CAAGATCGTTGGGAC-CTGGCC-3') and obsA Reverse Primer (SEQ ID NO:3 5'-TCGACGTACTGGACCTCGGC-3') resulted in a single PCR fragment equivalent to the 806-bp probe in size. PCR reactions were completed according to manufacturer's instruction using the FAILSAFE™ PCR System (Epicentre Biotechnologies, Madison, Wis.).

The DNA inserts carried by the four cosmid clones were also sequenced at both ends in order to map the cosmid clones onto the obscurin gene cluster and to estimate the insert size of the cosmid clones (FIG. 1). Cosmid clone 1E3 was determined to be 42,900 bp in size and contains the 5' end of obsA in the middle of the DNA insert. Cosmid clone 2N14 was determined to be 40,153 bp in size and does not carry the entire obsA coding region. The inserts in cosmid clones 3M23 and 4E16 contain the 5' end of obsA at one end and the DNA sequences beyond the obscurin gene cluster at the other end. The actual sizes of cosmid clones 3M23 and 4E16 were not estimated. Cosmid clone 1E3 was chosen for completing obsA disruption to determine the impact of polyketide synthase gene function abolishment on *S. spinosa* characteristics and spinosyn production.

Engineering the obsA Disruption Cosmid Clone Via PCR Targeting

To disrupt obsA within the obscurin gene cluster, the apramycin resistance disruption cassette (FRT-aac3(IV)-oriT-FRT) of plasmid pIJ773 (provided by the John Innes Center

Figure 2:
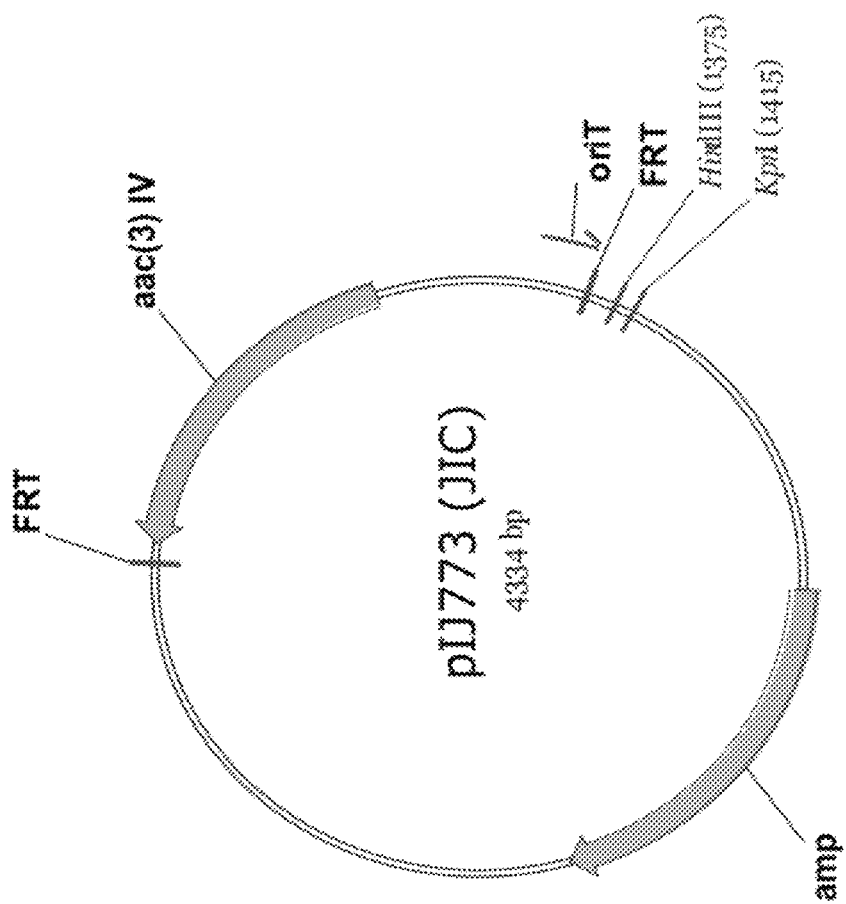
FIG. 2 depicts plasmid pI773 which contains the apramycin resistance expression cassette (labeled as aac(3) IV).

Plant Biosciences Limited, Norwich, England; FIG. 2) was integrated into cosmid clone 1E3 via PCR targeting.

Integration of the obsA disruption cassette (FRT-aac3(IV)-oriT-FRT) into cosmid clone 1E3 was carried out according to Gust et al. (2002) with the following modifications. The *E. coli* BW25141/pKD78 acquired from The Coli Genetic Stock Center (CGSC) at Yale University which contains the lambda red recombinase expression plasmid pKD78, derived from pKD46 (Datsenko and Wanner, 2000) was used. The following long PCR primers, ObsA 5' FRT aac3 (SEQ ID NO:4 5'-GGCAATGCGCAGAGTTCGTAGTGCGG-GAGCCATTTGATGTGTAGGCTGGAGCTG CTTC-3') and ObsA internal oriT FRT (SEQ ID NO:5 5'-GAAGAAG-GCGGCGTCGAACTGGTCGACCTCGGT-GAGGAAATTCCGGGGATCCGT CGACC-3'), were used for amplification of the 1322-bp fragment carrying FRT-aac3 (IV)-oriT-FRT using pIJ773 (FIG. 2) as template. The amplified fragment of 1,322 bp was purified and integrated into cosmid 1E3 according to Gust et al. (2002).

All ten of the recombinant *E. coli* clones which were produced from the PCR targeting were resistant to apramycin and had the same BamHI restriction enzyme digestion pattern (this digestion pattern is different from that of cosmid clone 1E3 not containing the disruption cassette). Further confirmation of the recombinant clones was carried out via amplification using a pair of primers annealing to the DNA regions 95 bp upsteam of the start codon of obsA and 334 bp downstream of the obsA start codon, respectively. The primers are obsA 5' upstream forward (SEQ ID NO: δ 5'-CGACCGGT-GTGTCGATGTTAGGGT-3') and obsA internal reverse (SEQ ID NO:7 5'-CTTCCAACGCTTCCCAGCCC-3'). PCR reactions were completed according to manufacturer's instruction using the FAILSAFE™ PCR System (Epicentre Biotechnologies, Madison, Wis.).

Amplification using either the genomic DNA of the spinosad strain used to created the cosmids or the DNA from cosmid clone 1E3 yielded the expected fragment of 429 bp. Amplification using the cosmid DNA isolated from nine (clone 10 was not pursued due to redundancy) of the ten recombinant cosmid clones yielded a single fragment corresponding to the expected size of 1,538 bp. The expected PCR fragment of 1,538 bp is due to the insertion of 1,322 bp of the disruption cassette (FRT-aac3(IV)-oriT-FRT) at the 5' end of obsA with simultaneous deletion of 213 bp from the obsA gene. All of the recombinant cosmid clones produced a single PCR fragment of 1,538 bp and did not produce the 429-bp fragment seen in the control cosmid clone 1E3 indicating that each of the recombinant cosmid clones contained the disruption cassette (FRT-aac3(IV)-oriT-FRT) at the 5' end of obsA. Disruption of ObsA within the Obscurin Gene Cluster Via Integration of the Disruption Cassette (FRT-aac3(IV)-oriT-FRT) in *S. spinosa*

Conjugation methods were used to introduce the recombinant cosmid clone carrying the obsA disruption cassette (FRT-aac3(IV)-oriT-FRT) into *S. spinosa* strains in order to achieve transconjugants from all of the target strains for conclusive analysis of the impact of obsA disruption on growth and spinosyn production.

Mycelial conjugation between the donor strain carrying the recombinant cosmid 1E3 and a recipient *S. spinosa* strain, NRRL 18538, was carried out according to the method described by Matsushima et al. (1994).

Transconjugants were produced. Nearly all of the primary transconjugants confirmed the desired apramycin-resistant phenotype indicating that the transconjugants carried the apramycin resistance gene, aac3(IV), integrated into the obscurin polyketide synthase gene cluster via homologous recombination. Several select transconjugants were tested for the presence of the DNA fragment corresponding to the size of a 785 bp aac3(IV) fragment upon PCR amplification. The negative controls which did not contain the disruption cassette (FRT-aac3(IV)-oriT-FRT) did not produce a PCR amplicon.

The Impact of obsA Disruption on *S. Spinosa* Growth and Spinosyn Production

The impact of obsA disruption on spinosyn production was evaluated using a spinosyn shake flask protocol. Fermentation of the transconjugants was performed under conditions described by Burns et al., (WO 2003070908). Analysis of the fermentation broth for the presence of spinosyn factors was carried out under conditions described by Baltz et al., (U.S. Pat. No. 6,143,526).

Direct comparison of the performance of the transconjugants relative to their respective parent strains was achieved for the *S. spinosa* isolates. Four of the obsA knockout mutants derived from strain NRRL 18538 were evaluated in shake flasks. The average titer of each knockout mutant was higher than the parent strain. However, the differences did not appear to be significant based on statistical analysis (Table 1).

TABLE 1

Spinosyn production at day 10 by the obsA knockout mutants derived from NRRL 18538.

| Strain | Major Spinosyn Factors | Spinosyn Titers Relative to Control in Percentage at Day 10 of Fermentation |
| --- | --- | --- |
| NRRL 18538 Parent | A/D | 100 |
| NRRL 18538 ΔobsA-1 | A/D | 108 |
| NRRL 18538 ΔobsA-2 | A/D | 114 |
| NRRL 18538 ΔobsA-3 | A/D | 108 |
| NRRL 18538 ΔobsA-6 | A/D | 107 |

The disruption of the obscurin PKS gene obsA in the A/D strain, NRRL 18538, had no negative impact on spinosyn production as compared to the respective parent control strains under current shake flask fermentation conditions. Lack of negative impact on spinosyn production upon obsA disruption qualifies the obscurin polyketide synthase gene cluster as a neutral site for integration and expression of target genes of interest for improved spinosyn production and fermentation processes. This genomic locus serves as an example of an integration site for the integration of genes within the genome of *S. spinosa*.

All patents and publications referenced are incorporated by reference herein in their entirety. The foregoing is illustrative of the present invention, and is not to be construed as limiting thereof. The invention is defined by the following claims, with equivalents of the claims to be included therein.

What is claimed is:

1. A method for producing spinosyn, the method comprising;
cloning two genomic DNA fragments from an obscurin polyketide synthase gene locus to generate a plasmid comprising a target gene, wherein one genomic fragment is cloned upstream of the target gene and the second genomic fragment is cloned downstream of the target gene;
integrating the plasmid comprising the target gene into a native obscurin polyketide synthase gene locus in a strain of *S. spinosa* to produce a strain of *S. spinosa* comprising the target gene;
culturing the strain of *S. spinosa* comprising the target gene;

allowing the strain of *S. spinosa* comprising the target gene to produce spinosyn; and expressing the target gene, wherein the target gene comprises a coding sequence functionally linked to a promoter heterologous to the strain of *S. spinosa*.

2. The method of claim 1, wherein the integration of the plasmid comprising the target gene into the native obscurin polyketide synthase locus of the strain of *S. spinosa* does not negatively impact spinosyn production, growth, or other desired metabolic characteristics.

3. The method of claim 1, wherein cloning two genomic DNA fragments from an obscurin polyketide synthase gene locus comprises cloning two genomic DNA fragments from an obsA obscurin polyketide synthase gene locus, and wherein integrating the plasmid comprising the target gene into a native obscurin polyketide synthase gene locus in a strain of *S. spinosa* comprises integrating the plasmid comprising the target gene into an obsA gene of the native obscurin polyketide synthase locus of the strain of *S. spinosa*.

4. The method of claim 1, wherein the target gene further comprises a selectable marker.

5. The method of claim 4, wherein the selectable marker comprises an apramycin resistance gene, aac3(IV).

6. The method of claim 1, wherein integration comprises a homologous recombination mediated integration.

7. A method for fermentation comprising:
cloning two genomic DNA fragments from an obscurin polyketide synthase gene locus to generate a plasmid comprising a target gene, wherein one genomic fragment is cloned upstream of the target gene and the second genomic fragment is cloned downstream of the target gene;
integrating the plasmid comprising the target gene into a native obscurin polyketide synthase gene locus in a strain of *S. spinosa* to produce a strain of *S. spinosa* comprising the target gene;
fermenting the strain of *S. spinosa* comprising the target gene;

allowing the strain of *S. spinosa* comprising the target gene to produce spinosyn; and expressing the target gene, wherein the target gene comprises coding sequence functionally linked to a promoter heterologous to the strain of *S. spinosa*.

8. The method of claim 7, wherein the integration of the plasmid comprising the target gene into the native obscurin polyketide synthase locus of the strain of *S. spinosa* does not negatively impact spinosyn production, growth, or other desired metabolic characteristics.

9. The method of claim 7, wherein cloning two genomic DNA fragments from an obscurin polyketide synthase gene locus comprises cloning two genomic DNA fragments from an obsA obscurin polyketide synthase gene locus, and wherein integrating the plasmid comprising the target gene into a native obscurin polyketide synthase gene locus in a strain of *S. spinosa* comprises integrating the plasmid comprising the target gene into an obsA gene of the native obscurin polyketide synthase locus of the strain of *S. spinosa*.

10. The method of claim 7, wherein the target gene further comprises a selectable marker.

* * * * *

SEQUENCE LISTING

<160> NUMBER OF SEQ ID NOS: 7

-continued

```
<210> SEQ ID NO 1
<211> LENGTH: 806
<212> TYPE: DNA
<213> ORGANISM: Saccharopolyspora spinosa

<400> SEQUENCE: 1
caagatcgtt gggacctggc cgcacgtttc gacgaggagc tttccggggcg ggggagcctg      60 gggtcgggcc gtggtggttt cctcaccgag gtcgaccagt tcgacgccgc cttcttcggg     120
atctcccctc gtgaagccgc cgaactcgac ccccggcagc ggctcacgct ggagctgggc     180
tgggaagcgt tggaagacgc cgggatcgtg ccgggtgcgc tgcgcggtga acgggtcgcc     240
gtgttcgtgg gcgcgatggg ggacgactac gccacgctga gcttcgccga cggcggctcc     300
cagatcggtc actacacggc gaccggtgtg cagcggagca tgatcgccaa ccggttgtcg     360
tacgtgctcg gtgtgcacgg cccgagcttc gtcgtcgact ccggtcagtc atcctccctg     420
gttgcggttc acctcgccgt ggagagcctg cgccgcggcg agtcttcggc cgccctggtc     480
ggcggggtca ccctgaacct ggctgcggag agcatggcgg ccacggccag gttcggcgcg     540 cttcgcccg acgggctctg cttcactttc gatgcacgcg cgaacggcta cgcacgcggt     600
gaaggcggcg gttcgccgt cctcaagccg ctgcacctcg cgctcggcga tggcgacgac     660
atctactgcg tgatccgcgg gaccgccatg aacaacgacg tggcggcga tgggctcacc     720 gtcccgaacg agcgcgccca gcaggcggtg ctcgcggagg cgtaccggcg agcgggagtg     780
gacccggccg aggtccagta cgtcga                                         806

<210> SEQ ID NO 2
<211> LENGTH: 21
<212> TYPE: DNA
<213> ORGANISM: Artificial Sequence
<220> FEATURE:
<223> OTHER INFORMATION: obsA Forward Primer

<400> SEQUENCE: 2
caagatcgtt gggacctggc c                                              21

<210> SEQ ID NO 3
<211> LENGTH: 20
<212> TYPE: DNA
<213> ORGANISM: Artificial Sequence
<220> FEATURE:
<223> OTHER INFORMATION: obsA Reverse Primer

<400> SEQUENCE: 3
tcgacgtact ggacctcggc                                                20

<210> SEQ ID NO 4
<211> LENGTH: 58
<212> TYPE: DNA
<213> ORGANISM: Artificial Sequence
<220> FEATURE:
<223> OTHER INFORMATION: ObsA 5' FRT aac3 Primer

<400> SEQUENCE: 4
ggcaatgcgc agagttcgta gtgcgggagc catttgatgt gtaggctgga gctgcttc       58

<210> SEQ ID NO 5
<211> LENGTH: 59
<212> TYPE: DNA
<213> ORGANISM: Artificial Sequence
<220> FEATURE:
<223> OTHER INFORMATION: ObsA internal oriT FRT Primer
```

-continued

```
<400> SEQUENCE: 5
gaagaaggcg gcgtcgaact ggtcgacctc ggtgaggaaa ttccggggat ccgtcgacc      59

<210> SEQ ID NO 6
<211> LENGTH: 24
<212> TYPE: DNA
<213> ORGANISM: Artificial Sequence
<220> FEATURE:
<223> OTHER INFORMATION: obsA 5' upstream forward Primer

<400> SEQUENCE: 6
cgaccggtgt gtcgatgtta gggt                                            24

<210> SEQ ID NO 7
<211> LENGTH: 20
<212> TYPE: DNA
<213> ORGANISM: Artificial Sequence
<220> FEATURE:
<223> OTHER INFORMATION: obsA internal reverse Primer

<400> SEQUENCE: 7
cttccaacgc ttcccagccc                                                 20
```